United States Patent [19]
Gal-Or et al.

[11] Patent Number: 6,059,949
[45] Date of Patent: May 9, 2000

[54] METHOD OF ELECTROPHORETIC DEPOSITION OF CERAMIC BODIES FOR USE IN MANUFACTURING DENTAL APPLIANCES

[75] Inventors: Leah Gal-Or, Haifa; Roni Goldner, Mizpe Adi; Liudmila Cherniak, Haifa; Nina Sezin, Haifa; Sonja Liubovich, Haifa, all of Israel

[73] Assignee: Cerel (Ceramic Technologies) Ltd., Nesher, Israel

[21] Appl. No.: 09/052,166

[22] Filed: Mar. 31, 1998

Related U.S. Application Data

[63] Continuation-in-part of application No. 08/839,047, Apr. 23, 1997, Pat. No. 5,919,347.

[51] Int. Cl.[7] .................................................. C25D 13/02
[52] U.S. Cl. ...................... 204/484; 204/491; 433/212.1; 433/222.1; 433/223
[58] Field of Search ..................... 204/490, 491, 204/484; 433/212.1, 222.1, 223, 206, 207

[56] References Cited

U.S. PATENT DOCUMENTS

| | | | |
|---|---|---|---|
| 4,246,086 | 1/1981 | Hennicke et al. | 204/491 |
| 4,557,591 | 12/1985 | Martin et al. | 433/202.1 |
| 4,879,136 | 11/1989 | Polz | 433/202.1 |

*Primary Examiner*—Kishor Mayekar
*Attorney, Agent, or Firm*—Mark M. Friedman

[57] ABSTRACT

A method for electrophoretic deposition of ceramic particles as a green body shaped as a dental appliance, the method comprising the steps of (a) forming a suspension of the ceramic particles in a first polar solvent, the ceramic particles constituting at least about 5% of the first suspension by weight; (b) passing a direct electrical current through the first suspension, using a deposition electrode shaped as the dental appliance to form a green body; (c) coating the green body with glass particles; and (d) sintering the resultant coated body for obtaining a glass coated all-ceramic dental appliance.

27 Claims, 1 Drawing Sheet

METHOD OF ELECTROPHORETIC DEPOSITION OF CERAMIC BODIES FOR USE IN MANUFACTURING DENTAL APPLIANCES

This is a continuation-in-part of U.S. patent application Ser. No. 08/839,047, filed Apr. 23, 1997 now U.S. Pat. No. 5,919,347.

FIELD AND BACKGROUND OF THE INVENTION

The present invention relates to electrophoretic deposition and, more particularly, to a method for the electrophoretic deposition of monolithic and laminated ceramic bodies coated with a layer of glass and shaped as dental appliances for dental restorations. Most specifically, the present invention relates to electrophoretic deposition of layers or composite of ceramic and glass particles to produce metal-free dental appliances, such as, but not limited to, crowns, artificial teeth and bridges, on a duplicate dental die obtained from a master model.

Precisely shaped, small ceramic bodies are used in many applications, including as pitch bonding capillaries in microelectronics, as high temperature nozzles, as ferrules for connecting optical fibers, as high temperature engine components, as dental appliances such as dental crowns, artificial teeth and bridges and as bearing parts.

To achieve the precise shaping required, some of these applications, e.g., bonding capillaries, it has been necessary to use the process of cold pressing to fabricate ceramic capillaries. To produce all-ceramic dental appliances a manual slip cast process is presently excercised.

Multilayer ceramic laminates, made of sequential layers of ceramics such as alumina and zirconia, are known in a variety of geometric shapes, including plates and discs. Applications of ceramic laminates include mechanical seals, automotive engine parts, furnace elements, multilayer and FGM substrates for hybrid circuits, capacitors, RF filters, and microwave components.

The processes used to fabricate ceramic laminates include chemical vapor deposition (CVD) and physical vapor deposition (PVD), for layers less than few microns in thickness; tape casting, for layers thicker than about 10 microns; and electrophoretic deposition (EPD), for layers between about 3 micron and about 100 microns in thickness, as will now be described.

Electrophoresis is a process in which charged ceramic particles suspended in a liquid medium are attracted to an electrode when an electrical field is imposed on the particles. EPD is the process of depositing a body of a desired shape on an electrode, using electrophoresis. EPD has long been used to form green ceramic bodies. In particular, EPD has been used by Sarkar, Haung and Nicholson (Electrophoretic deposition and its use to synthesize $Al_2O_3$/YSZ microlaminate ceramic composites, *Ceram. Eng. Sci. Proc.* vol. 14 pp. 707–716 (1993)) to deposit laminated composites of alumina and yttria-stabilized zirconia (YSZ).

Conventional ceramic dental appliances, such as crowns, artificial teeth and bridges consist of a metallic base covered with ceramic layers. All-ceramic (i.e., metal-free) dental appliances are highly desirable because they match the appearance of natural teeth better than metal-ceramic crowns do, they enable X-ray examination through the appliance and are more biocompatible, avoiding gum inflammations and allergic reactions.

Existing techniques for fabrication of all-ceramic dental appliances, the best known being the "Vita in-Ceram" method, are based on a manual slip cast process which requires high skills and does not exclude the formation of pinholes in the appliances prepared.

There is thus a widely recognized need for, and it would be highly advantageous to have, a method of EPD that can be used in the fabrication of small, precisely shaped ceramic bodies such as dental appliances, connecting ferrules, orifices and micro-tubes. Specifically, it would be highly advantageous to have a method of EPD that can be used in the fabrication of all-ceramic dental appliances

SUMMARY OF THE INVENTION

According to the present invention, there is provided a method for electrophoretic deposition of ceramic particles as a green body shaped as a dental appliance, including the steps of (a) forming a first suspension of the ceramic particles in a first polar (e.g., organic) solvent, the ceramic particles constituting at least about 5%, preferably at least 20%, or more, of the first suspension by weight; and (b) passing a first direct electrical current through the first suspension, using a deposition electrode shaped as the dental appliance. At any given time of the deposition process, the direct electrical current may have a constant voltage (e.g., between about 50 and about 400 volts) or a constant current density.

According to the present invention, there is provided a green body formed of ceramic particles and shaped as a dental appliance, such as an all-ceramic dental appliance. Preferably the green body is coated with a glass coat which is deposited either electrophoretically or by brushing.

If electrophoretic deposition is of choice, a suspension of glass particles is prepared preferably with a charging agent and it is deposited over a green body which serves as a core. In any case, the green body is preferably presintered at 1200° C. prior to deposition of the glass coat. After coating, the coated body is preferably sintered at 1100° C., such that the deposited glass melts and infiltrates into pores present in the particles composing the green body.

According to the present invention, there is provided a method for electrophoretic deposition of a mixture of ceramic particles and glass particles as a composite ceramic-glass green body, comprising the steps of (a) forming a first suspension of the ceramic and glass particles in a polar (e.g., organic) solvent, the ceramic and glass particles constituting at least about 5%, preferably at least 20%, or more, of the first suspension by weight; and (b) passing a direct electrical current through the suspension, using a deposition electrode. Composite bodies can be similarly coated with glass.

According to the present invention, there is provided an all-ceramic dental appliance comprising electrophoretically deposited ceramic particles, preferably further comprising a glass coating.

In the formation of ceramic green bodies by EPD, the ceramic particles may be positively charged, in which case they are deposited on the cathode; or they may be negatively charged, in which case they are deposited on the anode.

The electrode on which the ceramic particles are deposited is referred to herein as the "deposition electrode". In the examples given herein, the deposition electrode is the cathode, but it will be understood that the scope of the present invention includes the deposition by EPD of negatively charged ceramic and/or glass particles, so that the deposition electrode is the anode.

A small ceramic article such as a bonding capillary or a micro-tube is formed by deposition on a deposition electrode having an external shape identical to the desired internal shape of the capillary.

A dental appliance such as a crown, artificial tooth or bridge, is formed according to the present invention by deposition on a deposition electrode formed as a duplicate dental die coated with a conductive material. It may include a monolithic green body, a multilayer green body or a ceramic-glass composite green body. In any case, it is preferably deposited with a glass coat, preferably by electrophoretic deposition or by conventional brushing techniques, as herein described.

The green body must be sufficiently dense and rigid to retain its shape as it is removed from the deposition electrode and prepared for sintering or other processes. To achieve the necessary mechanical strength, the green body may be deposited on the deposition electrode in microlayers, as taught by Sarkar, Haung and Nicholson. This alone, however, is insufficient to give the green body the required rigidity.

Sarkar, Haung and Nicholson used suspensions that included up to 10% by weight of ceramic in polar organic liquids such as ethanol, and obtained green bodies with densities of about 60% of theoretical. Surprisingly, it has been found that using denser suspensions, including from about 20% to about 70% by weight of ceramic, allows the deposition by EPD of both laminated and monolithic green bodies, with densities of about 70% and higher of theoretical, that retain their shape when removed from the deposition electrode and sintered.

To achieve this green body density in a monolithic green body, it is necessary first to wash the ceramic powders repeatedly in a polar solvent such as deionized water, until the conductivity of the used washing solvent is essentially the same as the original conductivity of the washing solvent.

The utility of this washing step in the production of denser monolithic green bodies is believed to be related to the consequent reduction in the ionic conductivity of the suspension. This washing step is optional in the case of laminated green bodies. Preferably, the washed powders are dried before being added to the polar organic solvent to form the suspension.

Suspensions and slurries with higher concentrations of ceramic particles have been used to form green bodies by tape casting. For example, Chartier, Merle and Besson (Laminar ceramic composites, *J. Eur. Ceram. Soc.* Vol. 15 pp. 101–107 (1995)) used a slurry of greater than 60% ceramic in an azeotropic mixture of methyl ethyl ketone and ethanol to form alumina-zirconia laminates by tape casting. Tape casting is not suitable for fabricating the ceramic bodies of the present application, because, as noted above, tape casting is restricted in practice to layers thicker than about 100 microns, and to flat geometries. Kerkar et al., in U.S. Pat. No. 5,194,129, teach the manufacture of optical ferrules by EPD, using aqueous suspensions of ceramic particles that contained about 40% to 50% by weight of ceramic. Aqueous suspensions are not suitable for the present application because they are subject to electrolysis, leading to the formation of hydrogen bubbles at the cathode and a consequent decrease in the density and local uniformity of a green body deposited thereon.

A laminated green body is formed by EPD by using two or more suspensions of differing global compositions, and alternately placing the deposition electrode in each of the suspensions, until the desired number of microlayers is deposited. By "global composition" is meant the composition of the ceramic component of the suspension taken as a whole. For example, a suspension of 80% $Al_2O_3$ and 20% $ZrO_2$ has a different global composition than a suspension of 40% $Al_2O_3$ and 60% $ZrO_2$, even though the individual $Al_2O_3$ and $ZrO_2$ particles of the two suspensions are identical in composition. The microlayers are deposited at a constant current density, as taught by Sarkar, Haung and Nicholson, in order to achieve a constant rate of deposition.

The method of the present invention confers the following advantages on the resulting ceramic bodies (i) precisely controlled shape; (ii) uniform and parallel layers in laminates; (iii) High strength and toughness, in the case of multilayer laminates; (iv) fine, stress-free, defects-free microstructure; and (v) near net shaped products. In addition, the method is more cost effective and less wasteful of raw materials than other methods known in the art, is environment-friendly and can be automated in a straightforward manner.

Manufacturing ceramic elements, such as dental appliances, according to the present invention enjoys various advantages as compared with the prior art since the method of the present invention is simple, cost effective, lends itself to automation and thus eliminates the need for skilled personnel, while providing rigid control of article shape and dimensions. This method provides most accurate dental appliances or other articles featuring better microstructures, devoid of pinholes and with better mechanical and aesthetic properties and biocompatibility.

BRIEF DESCRIPTION OF THE DRAWINGS

The invention herein described, by way of example only, with reference to the accompanying drawing, wherein the sole FIGURE presents a cross sectional view of an EPD-cell assembly 10 suitable for practicing the method of the present invention.

The cell includes a EPD-cell 12 made of glass and equipped with a stirring mechanism which includes a magnetic stirrer 14 and a plastic coated magnet 16. Assembly 10 further includes a ring shaped counter electrode 18 (currently the anode) and a duplicated dental die formed from a master model as a deposition electrode 20 (currently the cathode), shown herein deposited. Assembly 10 further includes a timer 22 that controls the time periods of current supplied from a power supply 24 and monitoring instruments 26 such as voltmeter V and ampermeter A.

DESCRIPTION OF THE PREFERRED EMBODIMENTS

Figure 1:
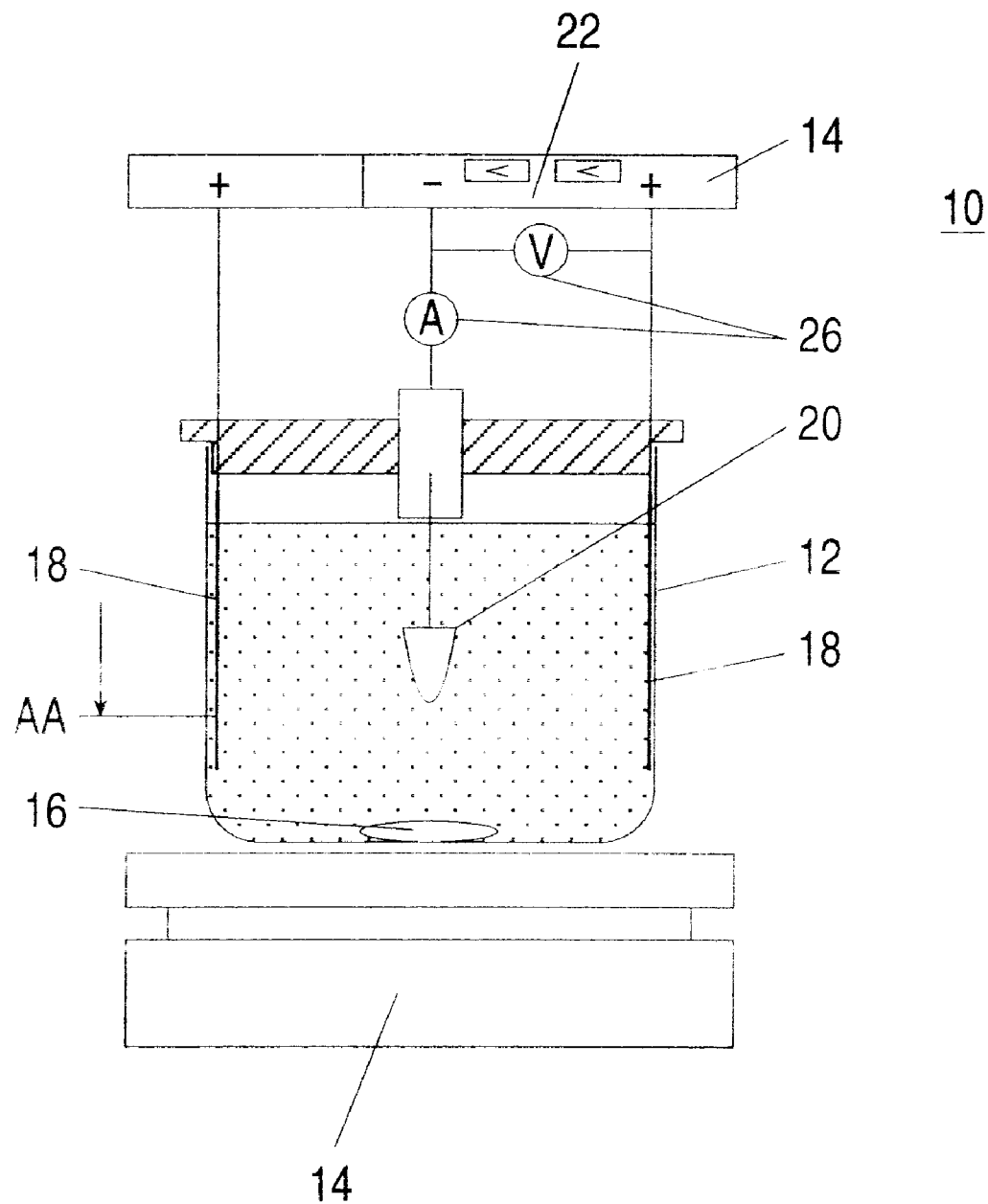

The present invention is of a method of electrophoretic deposition that can be used to form monolithic, multilayer or composite green bodies of precisely controlled shapes. Specifically, the present invention can be used in the fabrication of all-ceramic (i.e., metal-free) dental appliances such as crowns, artificial teeth and bridges.

The principles and operation of electrophoretic deposition according to the present invention may be better understood with reference to the following description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The scope of the present invention includes green and sintered bodies including electrophoretically deposited ceramics, both oxides and nonoxides.

Non-limitative examples of suitable ceramics include alumina (e.g., $Al_2O_3$), zirconia (e.g., $ZrO_2$), spinel (e.g., $MgAlO_4$), titania (e.g., $TiO_2$), baria (e.g., $Ba_2O_3$), calcia (e.g., CaO), silica (e.g., $SiO_2$), magnia (e.g., MgO) and mixtures thereof, such as, but not limited to, zirconia-toughened alumina and alumina-toughened zirconia and the like. If zirconia is selected it is preferably stabilized with yttria ($Y_2O_3$) ceria ($CeO_2$) and/or magnia (MgO), as well known in the art.

The particles should be small enough (typically less than about a few microns across) to produce a uniform deposit on the depositing electrode (e.g. cathode).

The preferred polar organic solvents are pure ethanol, pure methyl ethyl ketone, pure iso-propanol, pure acetone and mixtures thereof For some embodiments, a mixture ethanol and methyl ethyl ketone in ratios of between 50:50 and 80:20 is preferred. The most preferred solvent is the 60:40 azeotrope of ethanol and methyl ethyl ketone.

To impose the needed positive surface charge on the ceramic particles, the suspension is ball milled, using ceramic grinding media, for up to 24 hours, or subjected to 20 KHz ultrasound at a power level of up to about 550 watts, for between about 2 minutes and about 15 minutes, typically between about 4–5 minutes.

Optionally, additives such as pH adjustment agents, dispersants and binders are added to the suspension.

The pH adjustment agent can be any suitable organic or inorganic acid that is miscible in the polar organic solvent. The preferred pH adjustment agents are hydrochloric acid and acetic acid.

The preferred dispersants are acetylacetone, chloracetic acid, phosphate ester, triethanolamine and menhaden fish oil, some of which have been found to allow the deposition, in laminated green bodies, of relatively smooth ceramic microlayers as thick as about 100 microns, in contrast to the prior art microlayer thicknesses of no more than about 20 microns. The preferred dispersant for the fabrication of dental appliances are acetylacetone and phosphate ester.

It should be noted that the preferred microlayer thicknesses, to provide alumina-zirconia laminates of alternating alumina-rich and zirconia-rich layers with maximum strength and toughness, are between about 20 microns and about 40 microns, for the alumina-rich layer, and between about 30 microns and about 50 microns for the zirconia-rich layer.

The preferred binders are polyvinyl butyral (PVB), nitrocellulose and shellac.

The principle criteria for selecting electrode materials is that they be inert under process conditions and inhibit the evolution of hydrogen gas. If the deposition electrode is a cathode, it may be either consumable or reusable. A consumable cathode is one that is destroyed during the sintering process, so that the green body need not be removed from the cathode before sintering. The preferred materials for a consumable cathode are carbon and electrically conducting polymers.

The preferred materials for a reusable cathode are stainless steel, nickel, aluminum, tungsten carbide and noble metals such as platinum, palladium, silver and gold, their alloys, and non-conductive material featuring a conductive coating.

The preferred materials for the anode are nickel and noble metals.

In the production of small ceramic articles such as microtubes, the cathode is a wire having a shape identical to the desired interior shape of the ceramic article.

In the production of dental appliances the cathode is a duplicate dental die made of a hardened moldable material, such as gypsum or wax coated with a conductive paint such as silver paint (e.g., silver lacquer), or moldable conductive polymers. Preferably, the anode surrounds the cathode and preferably a cylindrical nickel anode is selected.

For best results, it is necessary to inhibit the production of hydrogen gas at the cathode. In addition to using a polar organic solvent instead of water to form the suspension, this is accomplished by including a hydrogen getter and/or a surface coating on the cathode to absorb hydrogen.

Preferred hydrogen getters include palladium and platinum and their alloys. In the case of stainless steel cathodes, a surface coating of a porous material such as porous tissue or paper has been found effective for both absorption of hydrogen and facilitating the removal of the green body from the cathode subsequent to the deposition. Removal of the green body from the cathode also is facilitated by polishing the cathode surface before deposition.

The anode and cathode are immersed in the suspension, and a direct electrical current of constant current density, as measured at the deposition electrode (e.g., the cathode), is passed between the electrodes while the suspension is stirred.

The preferred range of current densities is between about 0.1 $mA/cm^2$ and about 5 $mA/cm^2$, preferably about 0.1 $mA/cm^2$ and about 2 $mA/cm^2$. As noted above, to deposit a laminated green body, several suspensions of differing global composition are used, and the electrodes are moved from one suspension to another as necessary. The preferred range of voltage is about 50–400 volts.

The deposition time in each suspension depends on the desired microlayer thickness, the current density and the suspension concentration.

Typical deposition times for one microlayer range from a few seconds to a few minutes. The total deposition time for a planar laminated green body is on the order of a few hours.

The total deposition time for a monolithic or laminated cylindrical body, such as a pitch bonding capillary, having a diameter of a few millimeters is on the order of one minute or less.

The total deposition time for a monolithic or laminated dental appliance, such as a crown is on the order of 10–30 seconds.

According to one embodiment of the present invention, following the deposition, the green body is removed with or from the cathode, dried in a dessicator, and sintered. Pressureless sintering in air at about 1550° C. for a few hours has been found suitable for the production of stress-free alumina-zirconia laminates. The sintered ceramic body may be machined and/or polished after sintering.

However, according to another embodiment of the present invention, which embodiment was specifically developed for the production of dental appliances, following the deposition, the green body which forms a dental appliance core, is removed with or from the cathode, dried in air or a dessicator, then dried in a furnace up to 6–8 hours at 120° C. and thereafter the core is subjected to a presintering at about 1200° C. for, e.g., about 2 hours. As a result of presintering the porosity of the green body is reduced to some extent and its strength increases respectively. However, for reasons to be shortly described, at this stage some porosity is advantageous.

The core formed prior to, or preferably after presintering, is electrophoretically or otherwise deposited (e.g., by brushing according to the conventional techniques of applying external glass deposition to dental appliances) with a sintering temperature (e.g., above 500° C.) meltable substance, e.g., glass, and is thereafter subjected to liquid sintering (e.g., at 1100° C.) for a few hours, say 4 hours for glass impregnation of the ceramic core. If brushing is employed, an at least 10% by weight suspension of glass powder in water is preferred.

As a result, the sintering temperature meltable substance melts and infiltrates into the pores present in the core. When cooled, the sintering temperature meltable substance hardens as a layer externally deposited and coating the core. The coating layer is strongly engaged to the core due to the infiltration as described.

The following procedure is followed for electrophoretic deposition of the temperature meltable substance. A suspension including a temperature meltable substance powder such as glass is prepared in a polar organic solvent. For dental applications the preferred powder is glass, such as Vita glass B4.

The glass powder particles should be small enough (typically about a few microns across) to produce a uniform deposit on the depositing electrode (e.g., cathode).

As before, the preferred polar organic solvents are pure ethanol, pure methyl ethyl ketone, pure iso-propanol, pure acetone and mixtures thereof.

Charging agents such as nitrates of manganese $Mg(NO_3)$, yttrium $(YNO_3)$ and/or aluminum chloride $(AlCl_3)$, ammonia or barium oxide are added.

To impose the needed positive surface charge on the glass particles, the suspension is ball milled, using ceramic grinding media, for up to 24 hours, or subjected to 20 KHz ultrasound at a power level of up to about 550 watts, for between about 2 minutes and about 15 minutes, typically between about 1–5 minutes.

The core, either prior to, or preferably following presintering as described, is connected within an EPD-cell as described to serve as a deposited electrode, typically as a cathode. A direct electric current is passed through the cell. The preferred voltage range is 100–400 volts, and the preferred current range is about 0.1–2 $mA/cm^2$. The deposition time is of about 5 minutes.

According to yet another prefered embodiment of the present invention composite ceramic-glass green bodies are formed by co-deposition of ceramic and glass particles on a deposition electrode by electrophoretic deposition as hereinabove described, preferably followed by sintering. During sintering the glass particles melt and an internal glass structure is formed within pores of the ceramic particles. According to a preferred embodiment the ceramic and glass particles are deposited from a polar suspension of about 5–50% glass and ceramic particles by weight.

Manufacturing ceramic elements, such as dental appliances, according to the present invention enjoys various advantages as compared with the prior art. The method of the present invention is simple, cost effective, lends itself to automation and thus eliminates the need for skilled personnel, while providing rigid control of article shape and dimensions. In addition, this method provides most accurate dental appliances or other articles featuring better microstructures, devoid of pinholes and with better mechanical and aesthetic properties and better biocompatibility.

Reference is now made to the following examples, which together with the above descriptions, illustrate the invention in a non limiting fashion.

EXAMPLE 1

Multilayer Laminate

A first suspension was prepared by dispersing 270 grams of alumina powder (average particle size 0.4 microns) and 30 grams of zirconia powder (average particle size 0.3 microns) in 1000 ml of an azeotropic mixture of ethanol and methyl ethyl ketone.

A second suspension was prepared by dispersing 160 grams of the same alumina powder and 240 grams of the same zirconia powder in 1000 ml of an azeotropic mixture of ethanol and methyl ethyl ketone.

Both suspensions were prepared using 800 ml of the ethanol-methyl ethyl ketone mixture in each, and ball milled for 24 hours, using alumina balls to mill the first suspension and zirconia balls to mill the second suspension. 200 more ml of the ethanol-methyl ethyl ketone mixture was added to each suspension, to bring the total volume of solvent up to the desired 1000 ml. Enough HCl was added to each suspension to adjust the pH of the first suspension to about 7 and the pH of the second suspension to about 6.

About 0.5% by volume of acetylacetone dispersant was added to the first suspension.

About 1.5% by volume of acetylacetone dispersant was added to the second suspension.

About 0.1% by volume of shellac binder was added to each suspension. Each suspension now was transferred to its own electrophoretic cell.

The cathode was a stainless steel plate covered with Wattman lens paper.

Each electrophoretic cell was provided with its own half-cylinder nickel anode about 40 mm in radius.

The cathode was placed in the first electrophoretic cell at the center of curvature of the anode, and a direct electrical current having a current density of about 0.4 $mA/cm^2$ was passed between the electrodes for about 45 seconds.

The cathode then was removed from the first electrophoretic cell and placed in the second electrophoretic cell, at the same location as before relative to the anode, and the same 0.4 $mA/cm^2$ of direct electrical current was run between them.

This process was repeated for 50 cycles, resulting in the deposition of 100 microlayers, each about 50 microns thick, for a total laminate thickness of about 5 millimeters.

A final 50 micron alumina-rich microlayer was deposited in the first electrophoretic cell.

The green body was removed from the cathode, dried in a dessicator for a few hours, and sintered in air at 1550° C. for 4 hours.

A The green body had a density of about 70% of theoretical. The sintered body had an open porosity of between 0.2% and 0.5% by volume.

The microhardness of the alumina-rich microlayers, measured by the Vickers method, was about 2400 $kg/cm^2$. The microhardness of the zirconia-rich layers was about 2000 $kg/cm^2$. The bending strength of the sintered body was about 80 $kg/mm^2$.

EXAMPLE 2

Monolithic Capillary 45 grams of alumina (average particle size 0.4 microns to 0.5 microns) and 5 grams of zirconia (average particle size 0.3 microns) were washed repeatedly with deionized water until the conductivity of the wash water fell to about 5 microsiemens/cm.

The powders were dried, and enough ethanol was added to bring the total volume to 100 ml. The resulting suspension was ball milled for 4 hours. 0.025 ml of acetylacetone dispersant and 2 ml of a 5% by volume solution of shellac binder in ethanol were added.

The suspension was stirred for about 15 minutes and transferred to an electrophoretic cell.

Two different cathodes were used in two different runs: a graphite wire and a tungsten carbide wire having external shapes identical to the internal shape of a typical bonding capillary, tapering from a 1.2 millimeter diameter at the distal end to a 0.04 millimeter diameter at the proximal end.

The cathode was a nickel cylinder about 60 mm in diameter surrounding the cathode. The electrodes were placed in the electrophoretic cell and a direct electrical current having a current density of about 1.0 mA/cm$^2$ was run between them for about 60 seconds, resulting in the deposition of a 1 millimeter thick deposit.

The density of the deposited green bodies was about 70% of theoretical. The green body on the tungsten carbide cathode was removed, and the green bodies were sintered in air at 1550° C. for about 1.5 hours, yielding alumina capillaries with densities of 99% of theoretical and microhardnesses of 2500 kg/cm$^2$.

EXAMPLE 3
Electrophoretically Deposited Glass Coated Ceramic Bodies

A first suspension was prepared by suspending 25 grams of Al$_2$O$_3$ (average particle size 1–3 microns) in 100 ml of pure ethanol with addition of 0.05% vol.acetyl acetone and 0.1% vol. of 5% wt. PVB in pure ethanol.

A second suspension was prepared by dispersing 10 grams of glass powder in 100 ml pure ethanol with additives of nitrates of manganese and yttrium. Total concentration of nitrates was 0.25×1/10$^{-3}$ mol/liter at a 1:1 ratio. After sonication (4 minutes of the first suspension and 1 minute of the second suspension) each suspension was transferred into a dedicated EPD-cell. Each EPD-cell was provided with a cylindrical anode made of nickel.

A duplicate dental die made of gypsum coated with a silver paint served as a cathode in the cell containing the first suspension. An electric current was driven between the electrodes at 100 volts for 10–15 seconds. Then the ceramic core thus formed was dried in air followed by drying at 120° C. for 6 hours. Following the drying the core was presintered at 1200° C. for 2 hours.

The core thus obtained was then attached to a metal structure in the EPD-cell containing the second suspension to serve as a cathode and a current of 0.5 mA/cm$^2$ was driven between the core and the counter electrode at a voltage of 300 volts.

At this stage, the core was removed from the second suspension and dried in air for 5 hours, followed by sintering at 1100° C. for 2 hrs.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of manufacturing an all-ceramic dental appliance, the method comprising the steps of:
    (a) electrophoretically depositing at least one layer including ceramic particles on a deposition electrode, said at least one layer forming a green body having sufficient structural rigidity so as to serve in manufacturing the all ceramic dental appliance; and
    (b) removing said deposition electrode, thereby obtaining the all-ceramic dental appliance.

2. The method of claim 1, further comprising the step of depositing at least one layer of a sintering temperature meltable material on said green body.

3. The method of claim 2, wherein said sintering temperature meltable material is glass.

4. The method of claim 2, further comprising the step of sintering said green body.

5. The method of claim 4, wherein sintering is at 1100–1550° C.

6. The method of claim 2, wherein depositing said at least one layer of said sintering temperature meltable material on said green body is effected by electrophoretic deposition of said temperature meltable material on said green body.

7. The method of claim 6, wherein said temperature meltable material is deposited on said green body from a suspension including a polar solvent.

8. The method of claim 7, wherein said suspension further including a charging agent.

9. The method of claim 2, wherein depositing said at least one layer of said sintering temperature meltable material on said green body is effected by brushing a suspension containing said temperature meltable material onto said green body.

10. The method of claim 1, further comprising the step of presintering said green body.

11. The method of claim 10, wherein said presintering is effected at about 1200° C.

12. The method of claim 1, wherein said step of electrophoretically depositing said at least one layer including said ceramic particles on said deposition electrode is effected by a direct electrical current having at least one constant parameter selected from the group consisting of current density and voltage.

13. The method of claim 1, wherein said deposition electrode is a cathode.

14. The method of claim 13, wherein said step of electrophoretically depositing said at least one layer including said ceramic particles on said deposition electrode is effected by passing a direct electrical current between said deposition electrode and a counter electrode made of a material selected from the group consisting of noble metals and nickel.

15. The method of claim 1, wherein said deposition electrode is a duplicate dental die of a moldable material coated with a conductive paint.

16. The method of claim 15, wherein said moldable material is selected from the group consisting of gypsum, wax and polymers.

17. The method of claim 15, wherein said conductive paint is a silver paint.

18. The method of claim 1, wherein said step of electrophoretically depositing said at least one layer including said ceramic particles on said deposition electrode is effected by a direct electrical current having a current density between about 0.1 mA/cm$^2$ and about 5 mA/cm$^2$.

19. The method of claim 1, wherein said step of electrophoretically depositing said at least one layer including said ceramic particles on said deposition electrode is effected by a direct electrical current having a voltage of about 50 to about 400 volts.

20. The method of claim 1, wherein said ceramic particles are deposited from a suspension including at least one polar solvent.

21. The method of claim 20, wherein said at least one polar solvent is selected from the group consisting of a ketone and an alcohol.

22. The method of claim 1, wherein said ceramic particles are selected from the group consisting of alumina particles, zirconia particles, yttria-stabilized zirconia particles, ceria-stabilized zirconia particles, magnia-stabilized zirconia particles, titania particles, mixed alumina-zirconia particles, mixed alumina-titania particles, mixed zirconia-titania particles.

23. The method of claim 1, wherein said ceramic particles are deposited from a suspension including at least one a dispersant to said first suspension.

24. The method of claim 23, wherein said dispersant is selected from the group consisting of acetylacetone, chloracetic acid, phosphate ester, triethanolamine and menhaden fish oil.

25. The method of claim 1, wherein said at least one layer further includes co-electrophoretically deposited glass particles.

26. The method of claim 1, wherein said ceramic particles constituting at least about 5% of a suspension by weight.

27. The method of claim 1, wherein said deposition electrode is a consumable electrode.

* * * * *